US007697983B1

(12) United States Patent
Oza

(10) Patent No.: US 7,697,983 B1
(45) Date of Patent: Apr. 13, 2010

(54) IMPLANTABLE CARDIAC DEVICE AND METHOD OF OPTIMIZING STORAGE OF ELECTROPHYSIOLOGICAL DATA

(75) Inventor: Taral Oza, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 763 days.

(21) Appl. No.: 11/458,588

(22) Filed: Jul. 19, 2006

(51) Int. Cl.
*A61N 1/00* (2006.01)

(52) U.S. Cl. .......................................................... 607/5

(58) Field of Classification Search .................. 607/17, 607/19, 20; 600/529, 484, 547, 481, 509, 600/515; 375/257; 341/61; 369/124.13; 386/54

See application file for complete search history.

(56) References Cited

U.S. PATENT DOCUMENTS

| 4,827,259 A | 5/1989 | Murphy et al. |
|---|---|---|
| 5,215,098 A | 6/1993 | Steinhaus et al. |
| 5,255,186 A | 10/1993 | Steinhaus et al. |
| 5,323,309 A | 6/1994 | Taylor et al. |
| 6,454,719 B1 * | 9/2002 | Greenhut ..................... 600/484 |
| 6,473,008 B2 * | 10/2002 | Kelly et al. .................... 341/61 |
| 6,719,689 B2 | 4/2004 | Munneke et al. |
| 6,910,084 B2 * | 6/2005 | Augustijn et al. .............. 710/52 |
| 7,187,965 B2 * | 3/2007 | Bischoff et al. ............. 600/515 |
| 2002/0193663 A1 | 12/2002 | Munneke et al. |
| 2006/0094968 A1 * | 5/2006 | Drew ......................... 600/509 |

FOREIGN PATENT DOCUMENTS

| EP | 0526973 B1 | 11/1997 |
|---|---|---|
| WO | 0118973 A1 | 3/2001 |

* cited by examiner

*Primary Examiner*—George Manuel
*Assistant Examiner*—Robert N Wieland
(74) *Attorney, Agent, or Firm*—Steven M. Mitchell

(57) ABSTRACT

A method and device for collecting and storing electrophysiological data is presented. The method comprises: (a) sensing electrophysiological data from a patient; (b) classifying data intervals as either a critical interval or a non-critical interval; (c) identifying an episode; and (d) directing storage of the data representing the episode in the memory unit, wherein the data representing the episode is stored at varying sampling frequencies depending on the classification of the data interval. The device comprises a sense circuit, a processor, and a memory unit, wherein the processor is adapted to perform the above-stated method.

21 Claims, 4 Drawing Sheets

IMPLANTABLE CARDIAC DEVICE AND METHOD OF OPTIMIZING STORAGE OF ELECTROPHYSIOLOGICAL DATA

BACKGROUND OF THE INVENTION

1. Field of the Invention

The present invention relates generally to implantable devices. More specifically, the present invention relates to a method of optimizing storage of electrophysiological data in an implantable cardiac device.

2. Background Art

The heart is a series of pumps that are carefully controlled by an electrical system. This electrical system attempts to regulate the heart rate between 60 and 100 beats per minute (bpm). Abnormally fast heart rates are called tachycardias. As used herein, the term tachycardia means a heartbeat at a rate which is abnormally high and accordingly considered to be dangerous if permitted to continue, or any arrhythmia involving recognizable heartbeat patterns containing repetitions which are in excess of a periodic heartbeat within a safe range. When the ventricular chambers beat too quickly, the arrhythmia (i.e., unusual heart rhythm) is known as ventricular tachycardia (VT). When VT occurs, the ventricles may not be able to fill with enough blood to supply the body with the oxygen rich blood that it needs. Symptoms of VT include feeling faint, sometimes passing out, dizziness, or a pounding in the chest.

Ventricular fibrillation (VF) is a very fast and irregular heartbeat that is caused by abnormal impulses coming from several areas of the heart. These abnormal impulses take over the natural pacemaker function of the sinoatrial (SA) node. The heartbeat is so fast and irregular that the heart does not pump enough blood to the brain and body tissue, which may cause unconsciousness, or death.

Arrhythmias in the heart have typically been treated using electro-pacing or shock therapy. For example, when a patient's heart is found to be in VF, a jolting electrical pulse, or shock pulse, is delivered to the patient in order to reactivate the electrical signals throughout the heart. The shock pulse may be administered via external defibrillators, or via implantable cardioverter defibrillators (ICDs) configured to deliver such a shock.

ICDs, and other implantable cardiac devices, usually have memory storage units to record and store electrophysiological data from the patient. Specifically, data representing the time immediately before, during, and after an arrhythmia is stored for later analysis. Typically, devices use various ultra-break (polynomial based) compression algorithms to store the data. Compression algorithms allow storage of the data while effectively using minimum amounts of memory. However, compression algorithms require a lot of processing power from the device's battery in order to compress the data, hence reducing the longevity of the device. Also, compression algorithms often take a long time to compress the data, which introduces interaction problems with other critical processes in the device. Compression algorithms are also not effective for compressing noisy and high frequency signals.

What is needed is a method of optimizing storage of electrophysiological data in the memory unit of an implantable device.

BRIEF SUMMARY OF THE INVENTION

Presented herein is an implantable cardiac device comprising: a processor, a sense circuit coupled to the processor, and a memory unit coupled to the processor. The sense circuit is adapted to receive electrophysiological data from a patient's heart and deliver the data to the processor. The memory unit is adapted to store data received from the processor. The processor is adapted to classify data intervals as either an arrhythmia interval (critical interval) or a non-arrhythmia interval (non-critical interval), identify an arrhythmia episode, and direct storage of the data representing the arrhythmia episode in the memory unit. Further, the processor is adapted to direct the storage of the data representing the arrhythmia episode at varying sampling frequencies depending on the classification of the data interval. For example, the processor stores the data representing the arrhythmia interval at a first sampling frequency and the data representing the non-arrhythmia interval at a second sampling frequency; wherein the first sampling frequency is greater than the second sampling frequency. The first sampling frequency may be two or more times greater than the second sampling frequency. Further, the memory unit includes a buffer unit for storing streaming data and a permanent storage unit for storing the data representing the arrhythmia episode. In one embodiment, the device includes a telemetry unit adapted to deliver the stored data, or to stream real-time data, to an external device.

Also presented herein is a method of collecting and storing data in a memory unit of an implantable device, such as an implantable cardiac device, comprising: (a) sensing electrophysiological data from a patient; (b) classifying data intervals as either a critical interval or a non-critical interval; (c) identifying an episode; and (d) directing storage of the data representing the episode in the memory unit, wherein the data representing the episode is stored at varying sampling frequencies depending on the classification of the data interval. In one embodiment, step (d) further comprises: directing storage of the data representing the critical interval at a first sampling frequency and directing storage of the data representing the non-critical interval at a second sampling frequency, wherein the first sampling frequency is greater than the second sampling frequency. In one embodiment, the first sampling frequency may be two or more times greater than the second sampling frequency. In another embodiment, the method further comprises: (e) streaming the sensed data into a buffer division of the memory unit or to an external device in real-time which may further be transmitted over the internet; and (f) directing storage of the data representing the episode in a permanent storage division of the memory unit. In yet another embodiment, the method further comprises performing a compression algorithm on the data representing the episode.

BRIEF DESCRIPTION OF THE DRAWINGS/FIGURES

The accompanying drawings, which are incorporated herein, form part of the specification and illustrate an implantable cardiac device, and methods for collecting and storing data in a memory unit of the device. Together with the description, the drawings further serve to explain the principles of and to enable a person skilled in the relevant art(s) to make and use the device and methods presented herein. In the drawings, like reference numbers indicate identical or functionally similar elements.

DETAILED DESCRIPTION OF THE INVENTION

The following detailed description of an implantable device and methods of collecting and storing data in a memory unit of such a device refers to the accompanying drawings that illustrate example embodiments. Other embodiments are possible, and modifications may be made to the embodiments within the spirit and scope of the device and methods presented herein. Therefore, the following detailed description is not meant to be limiting. Further, it would be apparent to one of skill in the art that the device and methods, as described below, may be implemented in many different embodiments of hardware, software, firmware, and/or the entities illustrated in the figures. Any actual software, firmware, and/or hardware described herein is not limiting. Thus, the operation and behavior of the device and methods presented will be described with the understanding that modifications and variations of the embodiments are possible, given the level of detail presented.

Before describing the example methods in detail, it is helpful to describe an example environment in which they may be implemented. The methods presented herein are particularly useful in the environment of an implantable cardiac device. An implantable cardiac device is a medical device that is implanted in a patient to monitor electrical activity of a heart and to deliver appropriate electrical therapy; for example, pacing pulses, cardioverting pulses, or defibrillating (or shock) pulses, as required. The descriptions below are provided in specific relation to an implantable cardioverter defibrillator (ICD). However, the description of an ICD is used for exemplary purposes and the term "implantable cardioverter defibrillator" or simply "ICD" is not intended to be limiting. The methods presented are intended for use in any implantable device known in the art.

Figure 1:
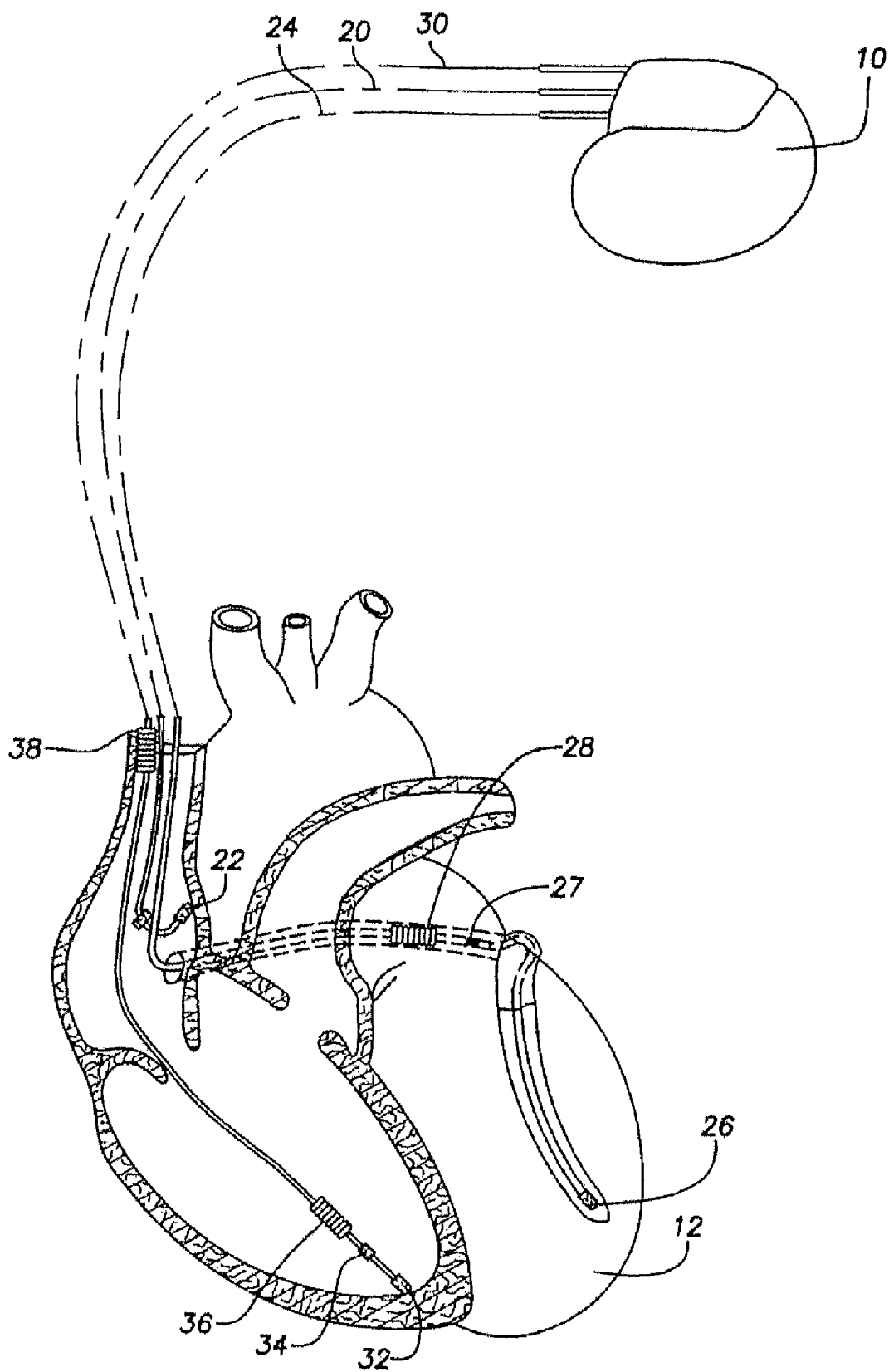
FIG. 1 is a simplified diagram illustrating an exemplary implantable cardioverter defibrillator (ICD) in electrical communication with a patient's heart.

FIG. 1 illustrates an exemplary ICD 10 in electrical communication with a patient's heart 12 by way of three leads 20, 24 and 30, suitable for delivering multi-chamber stimulation and pacing therapy. To sense atrial cardiac signals, and to provide right atrial chamber stimulation therapy, ICD 10 is coupled to implantable right atrial lead 20, having at least an atrial tip electrode 22, which typically is implanted near the patient's right atrial appendage.

To sense left atrial and ventricular cardiac signals, and to provide left chamber pacing therapy, ICD 10 is coupled to coronary sinus lead 24. Lead 24 is designed for placement in the coronary sinus region, via the coronary sinus, for positioning of a distal electrode adjacent to the left ventricle and/or additional electrode(s) adjacent to the left atrium. As used herein, the phrase coronary sinus region refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus. Accordingly, exemplary coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shock therapy using at least a left atrial coil electrode 28.

ICD 10 is also shown in electrical communication with the patient's heart 12 by way of an implantable right ventricular (RV) lead 30 having, in this embodiment, a RV tip electrode 32, a RV ring electrode 34, a RV coil electrode 36, and a superior vena cava (SVC) coil electrode 38. Typically, RV lead 30 is transvenously inserted into heart 12 so as to place the RV tip electrode 32 in the right ventricular apex so that RV coil electrode 36 will be positioned in the right ventricle and SVC coil electrode 38 will be positioned in the superior vena cava. Accordingly, RV lead 30 is capable of receiving cardiac signals and delivering stimulation in the form of pacing and shock therapy to the right ventricle. Other embodiments of ICD 10 may include a single electrode and lead or one or more alternative combinations of the above mentioned electrode and lead configurations. Additional embodiments of ICD 10 may include a fourth lead (not shown) extending from ICD 10 and having a physiological sensor, such as a pressure transducer, to monitor a physiological parameter, such as blood pressure and/or cardiac output, in any location within the cardiovasculature.

Amongst other things, any one of, or any combination of, leads 20, 24, and 30, functions as a sense circuit to sense and receive an electrogram (EGM) signal from the heart 12. The EGM signal is then processed within the ICD 10 processor (shown in FIG. 2), as discussed below. The sense circuit with respective electrodes, and the processor with respective circuitry, and equivalents thereof, thereby serve as means for detecting an arrhythmia in the patient's heart 12. Further, any one of, or any combination of the leads 20, 24, and 30, function as part of a therapy circuit to deliver a selected electro-therapy to the heart 12. The therapy circuit with respective electrodes, and the processor with respective circuitry, and equivalents thereof, thereby serve as means for delivering an electro-therapy, such as anti-tachycardia pacing (ATP) therapy or shock therapy, to the heart 12.

The selected electro-therapy can be, but is not limited to, ATP therapy or shock therapy. If ATP therapy is selected, a pre-programmed series of burst pulses is sent to the heart through any one of, or any combination of, leads 20, 24, and 30. There are several different ATP modalities which have been suggested for termination of tachycardia, with the underlying principle being to stimulate the heart (i.e., using a pacing pulse) at least once shortly after a heartbeat and before the next naturally occurring heartbeat at the rapid rate in an attempt to convert the tachycardia to sinus rhythm. Some examples of patent documents which discuss ATP therapies are U.S. Pat. No. 6,731,982, U.S. Pat. No. 4,408,606, U.S. Pat. No. 4,398,536, U.S. Pat. No. 4,488,553, U.S. Pat. No. 4,488,554, U.S. Pat. No. 4,390,021, U.S. Pat. No. 4,181,133 and U.S. Pat. No. 4,280,502, the disclosures of which are hereby incorporated herein in their entireties by reference.

Figure 2:
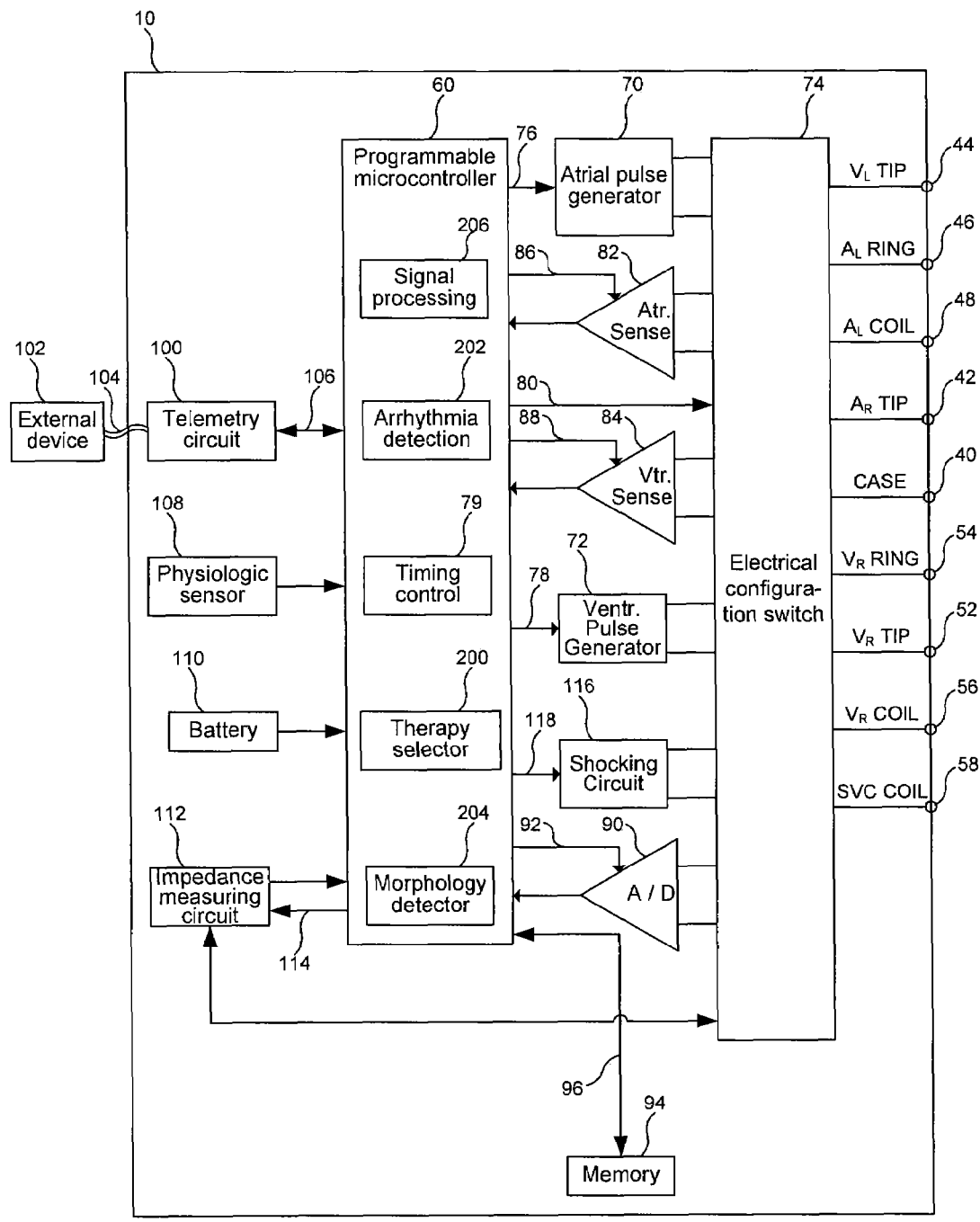
FIG. 2 is a functional block diagram of an exemplary ICD that can provide, amongst other things, cardioversion, defibrillation, and pacing stimulation in three chambers of a heart.

FIG. 2 shows a simplified block diagram of the dedicated circuitry included within ICD 10, which is capable of treating arrhythmias with stimulation therapy, including cardioversion, defibrillation, and pacing stimulation. While a particular block diagram is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation. As such, the presented block diagram is not intended to be limiting upon the appended claims.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes 28, 36, and 38, for shocking purposes. Housing 40 further includes a connector (not shown) having a plurality of terminals 42, 44, 46, 48, 52, 54, 56, and 58. These terminals are shown schematically and, for convenience, the names of the electrodes to which they are connected are shown next to the terminals. These terminals are only illustrative. ICD 10 may alternatively include more or less terminals, as deemed necessary by one skilled in the art.

As such, to achieve right atrial sensing and pacing, the connector includes at least a right atrial tip terminal ($A_R$ TIP) 42 adapted for connection to atrial tip electrode 22. To support right chamber sensing, pacing, and shocking the connector also includes a right ventricular tip terminal ($V_R$ TIP) 52, a right ventricular ring terminal ($V_R$ RING) 54, a right ventricular shocking terminal ($V_R$ COIL) 56, and an SVC shocking terminal (SVC COIL) 58, which are configured for connection to right ventricular tip electrode 32, right ventricular ring electrode 34, RV coil electrode 36, and SVC coil electrode 38, respectively. To achieve left chamber sensing, pacing, and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to left ventricular tip electrode 26, left atrial ring electrode 27, and left atrial coil electrode 28, respectively.

At the core of ICD 10 is a main processing unit, referred to as programmable microcontroller or simply processor 60, which controls the various modes of stimulation therapy. Microcontroller 60 typically includes a microprocessor, or equivalent control circuitry, designed specifically for controlling the delivery of stimulation therapy and can further include RAM or ROM, logic and timing circuitry, state machine circuitry, digital signal processing circuitry, and I/O circuitry. Known microcontrollers include the ability to process or monitor input data, such as biological signals, as controlled by a program code stored in a designated block of memory. The details of the design of microcontroller 60 are not critical to the present invention. Rather, any suitable microcontroller 60 can be used to carry out the functions described herein.

Representative types of control circuitry that may be used with the invention include the microprocessor-based control system of U.S. Pat. No. 4,940,052 and the state-machines of U.S. Pat. Nos. 4,712,555 and 4,944,298. For a more detailed description of the various timing intervals used within ICDs, and their inter-relationships, see U.S. Pat. No. 4,788,980. The '052, '555, '298 and '980 patents are incorporated herein by reference in their entireties.

Microcontroller 60 includes a timing control circuitry 79, which is used to control pacing parameters. Examples of pacing parameters include, but are not limited to, timing of stimulation pulses, burst pacing parameters, atrio-ventricular delay, interventricular delay, atrial interconduction delay, ventricular interconduction delay, and pacing rate. Amongst other things, timing control circuitry 79 is also used to keep track of the timing of refractory periods, post ventricular atrial refractory period intervals, noise detection windows, evoked response windows, alert intervals, and marker channel timing.

Microcontroller 60 also includes arrhythmia detection unit 202. Arrhythmia detection unit 202 includes programmable software, firmware, and/or hardware adapted to perform specific digital processing functions. Specifically, arrhythmia detection unit 202 is designed to classify the EGM data into data intervals. Typical data intervals can be, for example, one to six seconds in length. Each data interval is analyzed to identify the existence of an arrhythmia. As such, the interval is either classified as an "arrhythmia interval" or a "non-arrhythmia interval." By classifying and analyzing the data intervals, arrhythmia detection unit 202 is able to identify the inception of an arrhythmia and identify an arrhythmia episode. An "arrhythmia episode" is defined as the time interval and data that represent the occurrence of an arrhythmia in the patient's heart. The arrhythmia episode can include only the data representing the arrhythmia, or may include, for example, four to sixteen seconds of pre-arrhythmia data and up to thirty seconds of post-arrhythmia data. A typical arrhythmia episode is about thirty seconds; wherein the "critical data" is defined as the data within the arrhythmia episode which represents the actual arrhythmia. The length of the arrhythmia episode may vary in accordance with what a programmer may deem necessary.

Along with monitoring the heart rate, arrhythmia detection unit 202 may also serve the function of determining whether the heart rate is stable. Such physiological parameters may then be used to determine the necessary electro-therapy. If an arrhythmia is detected, typically based on heart rate, the arrhythmia may also be classified by morphology detector unit 204. Morphology detector unit 204, which also includes programmable software, firmware, and/or hardware adapted to perform specific digital processing functions, is adapted to classify the morphology of the patient's QRS complex as well as determine whether the QRS morphologies over consecutive QRS complexes are stable as would be known to one skilled in the relevant art. Finally, the arrhythmia is analyzed by therapy selector unit 200, in order to ultimately determine the type of electro-therapy needed, e.g., ATP, bradycardia pacing, cardioversion shocks, and/or burst pacing therapy. In deciding which electro-therapy is ultimately needed, therapy selector unit 200 receives and processes data from any one of, or any combination of, inputs including: a physiologic sensor 108, arrhythmia detection unit 202, and/or morphology detector unit 204.

Microcontroller 60 also includes a signal processing unit 206. Signal processing unit 206 includes programmable software, firmware, and/or hardware adapted to perform specific digital processing functions. Such functions may include, but are not limited to, digital signal compression. Compression of the digital signal may be performed by various algebraic, polynomial based, compression algorithms. Such compression is typically performed prior to permanent storage of the data. Signal processing unit 206 may also modify the data by varying the sampling frequency at which the data is stored or transmitted. As such, signal processing unit 206 is designed to adjust the resolution of the data before and/or after storage.

As shown in FIG. 2, ICD further includes an atrial pulse generator 70 and a ventricular pulse generator 72 to generate pacing stimulation pulses for delivery by right atrial lead 20, right ventricular lead 30, and/or coronary sinus lead 24 via an electrical configuration switch block 74. It is understood that in order to provide stimulation therapy, such as ATP therapy, in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses. As such, microcontroller 60, one or both pulse generators 70 and 72, switch block 74, and respective leads and electrodes, and any equivalents thereof, serve as means for delivering an ATP therapy to the heart of a patient.

Microcontroller 60 further controls a shocking circuit 116 by way of a control signal 118. Shocking circuit 116 generates shocking pulses of low, e.g., up to about 0.5 Joules, moderate, e.g., about 0.5-10 Joules, or high energy, e.g., about 11 to 40 Joules, as controlled by microcontroller 60. Such shocking pulses are applied to the patient's heart 12 through at least one electrode, e.g., selected from left atrial coil electrode 28, RV coil electrode 36, and SVC coil electrode 38 via switch block 74. As noted above, housing 40 may act as an active electrode in combination with RV coil electrode 36, or as part of a split electrical vector using SVC coil electrode 38 or left atrial coil electrode 28, i.e., using the RV electrode as a common electrode. Shocking circuit 116 typically includes at least one high-voltage capacitor. A "high-voltage capacitor" is defined as a capacitor designed, in isolation or in combination with at least one other capacitor, to provide the energy necessary to deliver a defibrillation shock. Shocking circuit 116 and associated capacitor, in combination with microcontroller 60, switch block 74, and associated leads and electrodes, and equivalents thereof, serve as means for delivering a shock therapy to the patient's heart.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level, i.e., corresponding to thresholds in the range of about 0.5-40 Joules, delivered asynchronously since R-waves may be too disorganized to be recognized, and pertaining exclusively to the treatment of fibrillation. Accordingly, software running on microcontroller 60 is capable of controlling the synchronous or asynchronous delivery of the shocking pulses.

Switch block 74 includes a plurality of switches for connecting the desired electrodes to the appropriate I/O circuits, thereby providing complete electrode programmability. Switch block 74 may include small, high-voltage switching transistors, known in the art as insulated gate bipolar transistors (IGBT). Accordingly, switch block 74, in response to a control signal 80 from microcontroller 60, determines the types of stimulation pulses and the polarity of the stimulation pulses, e.g., unipolar, bipolar, combipolar, etc., by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch block 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch block 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60, which in turn is able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84. For arrhythmia detection, ICD 10 utilizes the atrial and ventricular sensing circuits 82 and 84 to retrieve EGM signals from the heart. The EGM signals are then analyzed in the arrhythmia detection unit 202 of the microcontroller 60.

Cardiac signals are also applied to the inputs of an analog-to-digital (A/D) data acquisition system 90. Data acquisition system 90 is configured to acquire EGM signals, convert the raw analog data into a digital signal, and deliver the digital signals to microcontroller 60 for later processing. Data acquisition system 90 is coupled to right atrial lead 20, coronary sinus lead 24, and right ventricular lead 30, through switch block 74, to sample cardiac signals across any pair of desired electrodes.

Advantageously, data acquisition system 90 can be coupled to microcontroller 60, or other detection units, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90, via a control signal 92, to sample the cardiac signal that falls in the capture detection window and, based on the amplitude, determine if capture has occurred.

The implementation of capture detection circuitry and algorithms are well known. See for example, U.S. Pat. No. 4,729,376, U.S. Pat. No. 4,708,142, U.S. Pat. No. 4,686,988, U.S. Pat. No. 4,969,467, and U.S. Pat. No. 5,350,410, which patents are hereby incorporated in their entireties herein by reference. The type of capture detection system used is not critical to the present invention.

Microcontroller 60 is further coupled to a memory unit 94 by a suitable data/address bus 96. Memory unit 94 may be used to permanently store EGM data. The term "permanently store" is used to indicate long-term storage and should not be interpreted to mean that the data cannot be removed or erased when appropriate. In contrast, memory unit 94 may also be used for buffer storage of EGM data. The term "buffer storage" is known to mean temporary storage of streaming data; wherein once the buffer is full, the oldest data is overwritten by new data. As such, memory unit 94 serves the dual functions of: a) providing a temporary storage for data while analysis and processing is performed by microcontroller 60; and b) providing permanent storage for processed data until it is downloaded or delivered to a physician for analysis.

The programmable operating parameters used by microcontroller 60 are also stored in memory unit 94. Such operating parameters are stored and modified, as required, in order to customize the operation of ICD 10 to suit the needs of a particular patient. Operating parameters define, for example, pacing pulse amplitude, pulse duration, electrode polarity, rate, sensitivity, automatic features, arrhythmia detection criteria, and the amplitude, and wave shape and vector of each shocking pulse to be delivered to heart 12 within each respective tier of therapy. The memory unit 94 thus serves as means for "learning" which therapies are most effective under certain conditions. As such, when a condition repeats itself, the memory can recognize the condition and adapt the selected therapy to match the previously used successful therapy.

Advantageously, the operating parameters of ICD 10 and microcontroller 60 may be non-invasively programmed into memory unit 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 also allows EGM data and status information relating to the operation of ICD 10, as contained in microcontroller 60 or memory 94, to be sent to external device 102 through established communication link 104. For examples of such external devices, see U.S. Pat. No. 4,809,697, U.S. Pat. No. 4,944,299, and U.S. Pat. No. 6,275,734, all patents being hereby incorporated in their entireties herein by reference. Telemetry circuit 100 also serves as a means for receiving control parameters from an outside programmer, to thereby program the microcontroller 60.

ICD 10 further includes a physiologic sensor 108 that can be used to detect changes in cardiac performance or changes in the physiological condition of the patient. Accordingly, microcontroller 60 can respond by adjusting the various pacing parameters such as amplitude, rate, AV Delay, RV-LV Delay, V-V Delay, etc., or electro-therapy delivered such as ATP therapy or shock therapy. Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead, which can be placed inside or outside the bloodstream, and coupled to microcontroller 60 through switch block 74.

Physiological sensor 108 may be, but is not limited to, a posture sensor such as an accelerometer, an inertial sensor, or a rate gyroscope, a pressure transducer, an impedance sensor, a blood velocity sensor, a respiratory sensor, or a sensor which measures the oxygen content in a patient's blood. Thus, for example, if the intention is to monitor the physiological parameter of the patient's posture, physiological sensor 108 would be a posture sensor, such as an accelerometer, an inertial sensor, or a rate gyroscope, located either internal or external to ICD 10. As such, physiological sensor 108 would monitor whether the patient is upright, horizontal, wobbling, or whether there is a quick change from an upright position to a hunched-over position. Alternatively, if the intention is to monitor the physiological parameter of cardiac output, physiological sensor 108 may be a pressure transducer, an impedance sensor, a blood velocity sensor, a respiratory sensor, or a sensor which measures the oxygen content in a patient's blood. As such, physiological sensor 108 is adapted to monitor cardiac output using any of the cardiac output measuring techniques known in the art.

ICD 10 may further include a magnet detection circuitry (not shown), coupled to microcontroller 60. The magnet detection circuitry detects when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 is shown as having an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement, detecting operable electrodes and automatically switching to an operable pair if dislodgement occurs, measuring respiration or minute ventilation, measuring thoracic impedance for determining shock thresholds, detecting when the device has been implanted, measuring stroke volume, and detecting the opening of heart valves. The impedance measuring circuit 112 is advantageously coupled to switch block 74 so that any desired electrode may be used. The impedance measuring circuit 112 is not critical to the present invention and is shown only for completeness.

ICD 10 additionally includes a battery 110, which provides operating power to a load that includes all of the circuits shown in FIG. 2. Battery 110 also serves to charge the high-voltage capacitor coupled to shocking circuit 116, which is used to deliver the high-voltage shock to the patient. Battery 110, and equivalents thereof, serves as a means for charging a high-voltage capacitor. Exemplary batteries include SVO or $MnO_2$ high rate batteries, either in rolled or flat electrode configurations.

Figure 3:
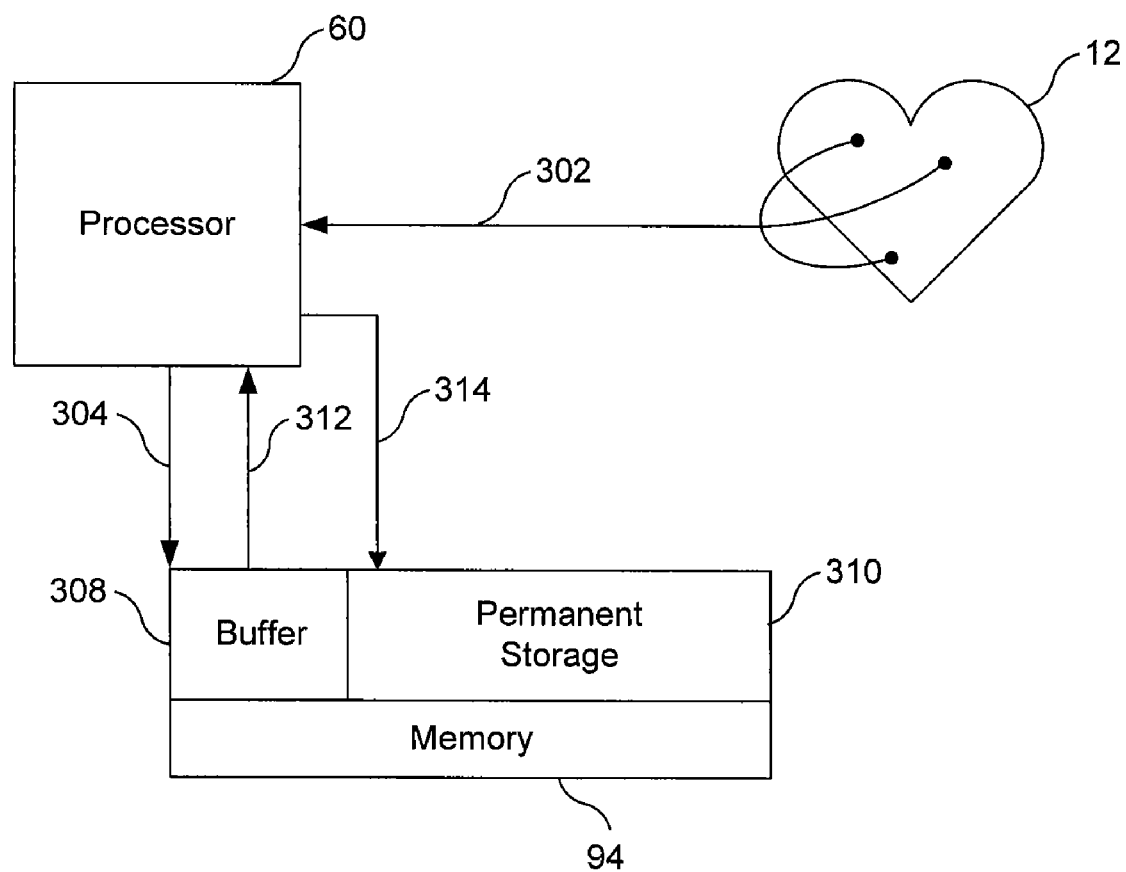
FIG. 3 is a high-level block diagram showing collection and storage of data in a memory unit of an implantable cardiac device.

FIG. 3 is a high-level block diagram showing collection and storage of data in a memory unit of an implantable cardiac device. As shown in FIG. 3, a processor, such as previously described microcontroller 60, receives electrical signals from the heart 12 through sense circuit 302. Processor 60 then delivers unprocessed or uncompressed data to memory unit 94 as represented by data stream 304. Memory unit 94 is divided between a buffer unit 308 and a permanent storage unit 310. Buffer region 308 is adapted to receive streaming data. When processor 60 detects an arrhythmia, it retrieves data from buffer 308 as represented by data stream 312. From there, processor 60 can properly analyze the data and identify an arrhythmia episode. Processor 60 then compresses the data and returns the data to memory 94 as represented by data stream 314. Upon return of the processed data to memory 94, the data is stored in permanent storage unit 310 of memory 94. The data stored in the permanent storage unit 310 is preferably stored at varying sampling frequencies depending on the classification of the data interval. For example, data classified as representing an arrhythmia interval (critical data) may be stored at a first sampling frequency, while data representing a non-arrhythmia interval (non-critical data) may be stored at a second sampling frequency. The first sampling frequency is generally greater than the second sampling frequency. For example, the first sampling frequency may be two or more times greater than the second sampling frequency.

Figure 4:
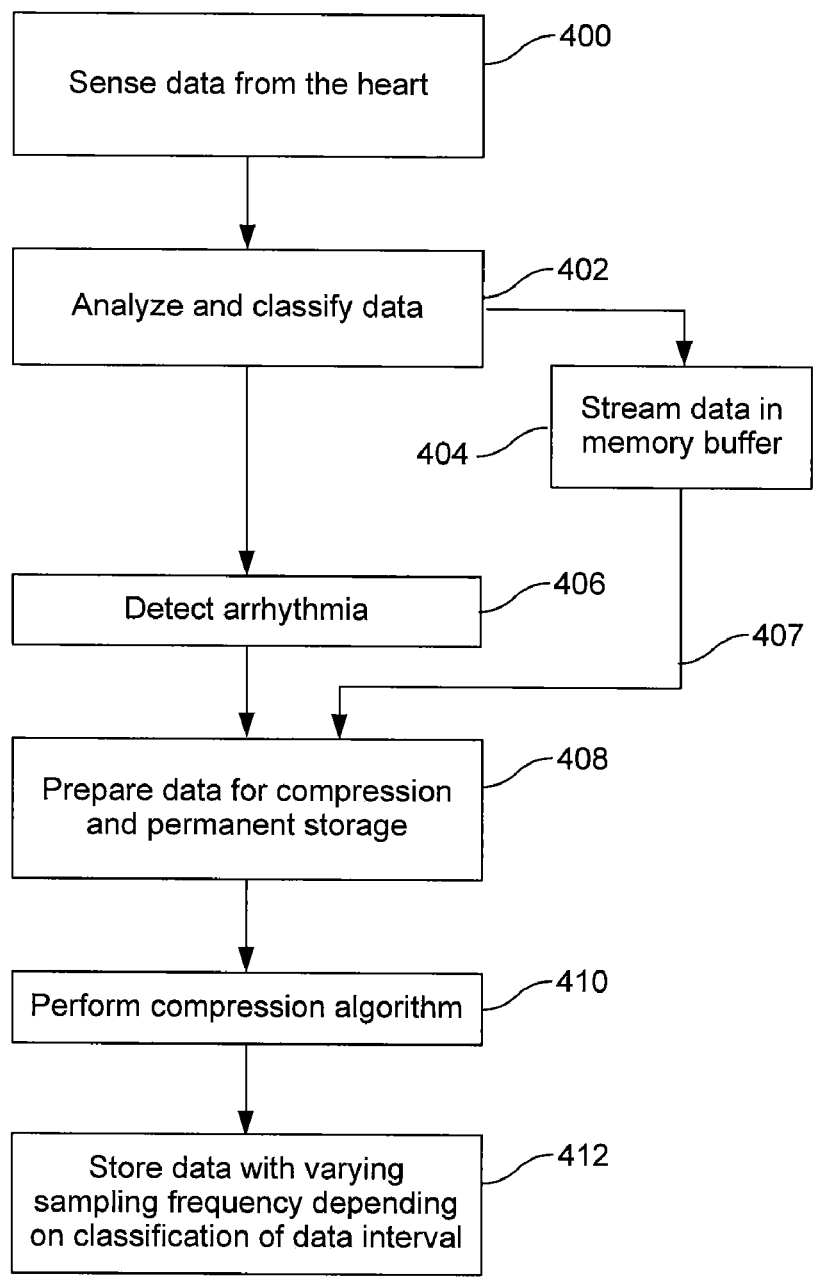
FIG. 4 is a flowchart showing a method of collecting and storing data in a memory unit of an implantable cardiac device.

FIG. 4 is a flowchart showing a method of collecting and storing data in a memory unit of an implantable cardiac device. In step 400, data is sensed from the heart of the patient. Step 400 is performed by any of the hardware described above as a sensing circuit. The data is then analyzed and classified in step 402. Step 402 is typically performed in, for example, microcontroller 60 as described above. While the data is being analyzed and classified by the software running on microcontroller in step 402, in a parallel process, streaming data is delivered to the buffer unit of the device's memory in step 404. Upon detection by microcontroller 60 of an arrhythmia, in step 406, data is returned from the buffer in step 407.

In step 408, the data is prepared for compression and permanent storage. Such preparation includes the determination of the arrhythmia episode and the critical data within the arrhythmia episode. As stated above, the arrhythmia episode my include data immediately before, during and after the arrhythmia. Further, the sampling frequency for the critical data and the non-critical data is determined in step 408. An optional compression algorithm is performed in step 410. The compression algorithm of step 410 is preferably performed on only the critical data, but can be performed on both the critical and non-critical data of the arrhythmia episode.

After compression, the data is stored with varying sampling frequencies depending on the classification of the data interval. Such directed storage is performed in step 412. In essence, non-critical data is stored at a lower sampling frequency than critical data. As such, the resolution of the critical data is higher. For example, the critical data may be stored at the original sampling frequency, thereby not sacrificing any resolution of the critical data. The non-critical data, however, can be down-sampled by a factor of n, where $n=2, 3, \ldots, f$. As such, resolution of the non-critical data is sacrificed for the advantages of memory space, processing time, battery consumption, etc.

The method presented is applicable to any intrinsic or surface channel which collects IEGM or surface ECG signal where the interval classification information is available to the signal storage algorithm, or to the real-time signal streaming algorithm, for each interval. This method can be implemented by itself (i.e, standalone) or in conjunction with existing compression algorithms. When implemented standalone, it can provide, for example, storage optimization equivalent to about 50% compression value for $n=2$ in the above description. When an external instrument retrieves the available EGM data for diagnostic purposes in the clinic, the data can be plotted with non-uniform sampling rates. This can also be done by converting the down-sampled data into a signal with the original sampling frequency by using any frequency conversion algorithm available. However, since the down-sampling is done for information that is not clinically relevant, frequency conversion may not be of any advantage. It is recommended that the external instrument simply plot the data with a non-uniform sampling rate to simplify the implementation and expedite execution.

CONCLUSION

The presented method may be implemented various different ways, with a general purpose being to down-sample the data intelligently to avoid any loss of information which is of significance. While example embodiments have been described, these example embodiments have been described for illustrative purposes only, and are not limiting. Other embodiments are possible and are covered by the device and methods described herein. Such embodiments will be apparent to persons skilled in the relevant art(s) based on the teachings contained herein. The scope of the present invention is solely defined by the following claims.

What is claimed is:

1. An implantable cardiac device comprising:
   a processor;
   a sense circuit coupled to the processor and adapted to receive electrophysiological data from a patient's heart and deliver the data to the processor; and
   a memory unit coupled to the processor and adapted to store data received from the processor;
   wherein the processor is adapted to classify data intervals as either an arrhythmia interval or a non-arrhythmia interval, identify an arrhythmia episode, and direct storage of the data representing the arrhythmia episode in the memory unit, wherein data intervals representing the arrhythmia episode are stored at varying sampling frequencies depending on classification as either arrhythmia interval or non-arrhythmia interval.

2. An implantable cardiac device as defined in claim 1, wherein the memory unit includes a buffer unit and a permanent storage unit.

3. An implantable cardiac device as defined in claim 2, wherein the data stored at varying sampling frequencies is stored in the permanent storage unit of the memory.

4. An implantable cardiac device as defined in claim 1, further including a telemetry unit adapted to deliver stored data to an external device.

5. An implantable cardiac device as defined in claim 1, further including a telemetry unit adapted to stream real-time data to an external device.

6. An implantable cardiac device as defined in claim 1, wherein the processor is adapted to store the arrhythmia interval at a first sampling frequency and the non-arrhythmia interval at a second sampling frequency, and wherein the first sampling frequency is greater than the second sampling frequency.

7. An implantable cardiac device as defined in claim 6, wherein the first sampling frequency is two times greater than the second sampling frequency.

8. An implantable cardiac device as defined in claim 6, wherein the first sampling frequency is at least three times greater than the second sampling frequency.

9. A method of collecting and storing data in a memory unit of an implantable cardiac device comprising:
   (a) sensing electrophysiological data from a patient's heart;
   (b) classifying data intervals as either an arrhythmia interval or a non-arrhythmia interval;
   (c) identifying an arrhythmia episode; and
   (d) directing storage of the data intervals representing the arrhythmia episode in the memory unit, wherein the data intervals representing the arrhythmia episode are stored at varying sampling frequencies depending on classification as either arrhythmia interval or non-arrhythmia interval.

10. A method as defined in claim 9, further comprising:
    (e) streaming data into a buffer division of the memory unit.

11. A method as defined in claim 10, further comprises:
    (f) directing storage of data representing the arrhythmia in a permanent storage division of the memory unit.

12. A method as defined in claim 9, wherein step (d) further comprises:
    directing storage of the data representing the arrhythmia interval at a first sampling frequency and directing storage of the data representing the non-arrhythmia interval at a second sampling frequency, wherein the first sampling frequency is greater than the second sampling frequency.

13. A method as defined in claim 12, wherein the first sampling frequency is two times greater than the second sampling frequency.

14. A method as defined in claim 12, wherein the first sampling frequency is at least three times greater than the second sampling frequency.

15. A method as defined in claim 9, further comprising:
    (e) performing a compression algorithm on the data representing the arrhythmia episode.

16. A method of collecting and storing data in a memory unit of an implantable device comprising:
   (a) sensing electrophysiological data from a patient;
   (b) classifying data intervals as either a critical interval or a non-critical interval;
   (c) identifying an episode; and
   (d) directing storage of the data intervals representing the episode in the memory unit, wherein the data intervals representing the episode are stored at varying sampling frequencies depending on classification.

17. A method as defined in claim 16, further comprising:
   (e) streaming the sensed data into a buffer division of the memory unit; and
   (f) directing storage of the data representing the episode in a permanent storage division of the memory unit.

18. A method as defined in claim 16, wherein step (d) further comprises:
   directing storage of the data representing the critical interval at a first sampling frequency and directing storage of the data representing the non-critical interval at a second sampling frequency, wherein the first sampling frequency is greater than the second sampling frequency.

19. A method as defined in claim 18, wherein the first sampling frequency is two times greater than the second sampling frequency.

20. A method as defined in claim 18, wherein the first sampling frequency is at least three times greater than the second sampling frequency.

21. A method as defined in claim 16, further comprising:
   (e) performing a compression algorithm on the data representing the episode.

* * * * *